US006902705B1

(12) United States Patent
Caillat et al.

(10) Patent No.: US 6,902,705 B1
(45) Date of Patent: Jun. 7, 2005

(54) DEVICE COMPRISING A PLURALITY OF ANALYSIS SITES ON A SUPPORT

(75) Inventors: Patrice Caillat, Echiolles (FR); Charles Rosilio, Gif sur Yvette (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/805,772

(22) PCT Filed: Sep. 15, 1999

(86) PCT No.: PCT/FR99/02191
§ 371 (c)(1),
(2), (4) Date: Mar. 16, 2001

(87) PCT Pub. No.: WO00/16082
PCT Pub. Date: Mar. 23, 2000

(30) Foreign Application Priority Data

Sep. 16, 1998 (FR) .............................................. 98 11561

(51) Int. Cl.$^7$ ................................................. B01L 3/00
(52) U.S. Cl. ...................... 422/102; 422/99; 435/283.1; 435/288.3; 435/288.4; 435/287.9
(58) Field of Search .......................... 422/681, 99, 102, 422/942; 436/174, 180; 435/283.1, 287.9, 288.4; 356/244, 246, 337

(56) References Cited

U.S. PATENT DOCUMENTS

| | | | | | |
|---|---|---|---|---|---|
| 4,231,660 | A | * | 11/1980 | Remy et al. .................. | 356/244 |
| 4,705,705 | A | * | 11/1987 | Bross .......................... | 428/13 |
| 5,474,796 | A |   | 12/1995 | Brennan | |
| 5,639,671 | A | * | 6/1997 | Bogart et al. ................ | 436/518 |
| 5,653,939 | A |   | 8/1997 | Hollis et al. | |
| 5,985,551 | A | * | 11/1999 | Brennan ....................... | 435/6 |
| 6,027,695 | A | * | 2/2000 | Oldenburg et al. .......... | 422/102 |
| 6,103,479 | A | * | 8/2000 | Taylor ......................... | 435/7.2 |
| 6,121,048 | A | * | 9/2000 | Zaffaroni et al. ............. | 436/45 |
| 6,289,144 | B1 | * | 9/2001 | Neuschafer et al. .......... | 385/12 |
| 6,410,675 | B2 | * | 6/2002 | McGall et al. ................ | 528/10 |
| 6,565,813 | B1 | * | 5/2003 | Garyantes ................... | 422/102 |
| 6,573,338 | B2 | * | 6/2003 | Halverson et al. .......... | 525/375 |

FOREIGN PATENT DOCUMENTS

WO    WO 96/28538    9/1996

OTHER PUBLICATIONS

R. J. Jackman, et al., Analytical Chemistry, vol. 70, No. 11, pp. 2280–2287, "Fabricating Large Arrays of Microwells with Arbitrary Dimensions and Filling Them Using Discontinuous Dewetting", Jun. 1, 1998.

M. Eggers, et al., IEEE, pp. 87–92, "A Versatile Biochip for Gene–Based Diagnostics", 1996.

K. Beattie, et al., Clinical Chemistry, vol. 39, No. 34, pp. 719–722, "Genosensor Technology", 1993.

* cited by examiner

*Primary Examiner*—Jill Warden
*Assistant Examiner*—Dwayne K Handy
(74) *Attorney, Agent, or Firm*—Oblon, Spivak, McClelland, Maier & Neustadt, P.C.

(57) ABSTRACT

The subject of the invention is a device for chemical or biological analysis comprising a carrier (21) containing a plurality of analysis sites able to fix a chemical or biological reagent, in which the analysis sites are formed of microdishes (23) hollowed out of the carrier, the side walls and the bottom of the microdishes and the areas of the carrier surface surrounding each microdish, called microdish edges, being made in at least one hydrophilic material (24), and the planar areas of the carrier arranged between the areas surrounding the microdishes being made in a hydrophobic material (27).

Drops (29) of reagent are therefore guided into the microdishes (23) on account of the hydrophobic areas (27). It is therefore possible to increase the density of analysis sites on the carrier.

17 Claims, 7 Drawing Sheets

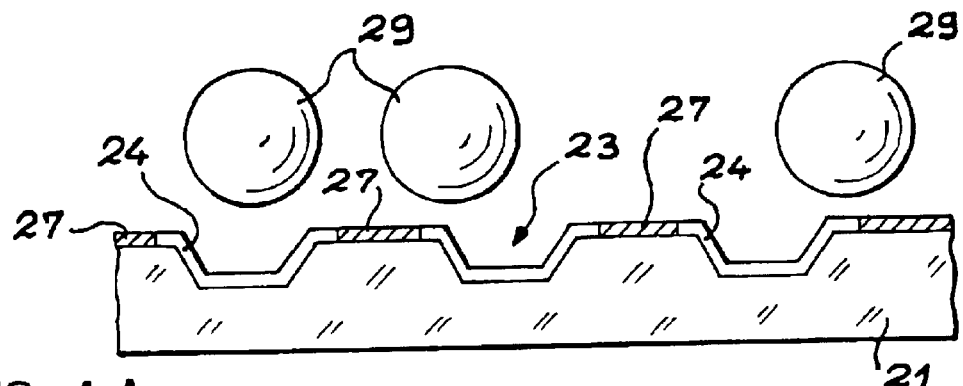
FIG. 4 A
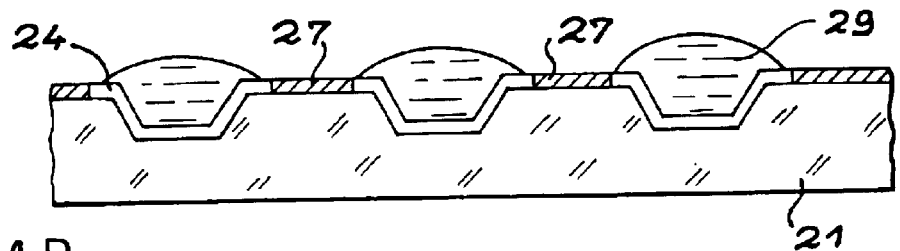
FIG. 4 B
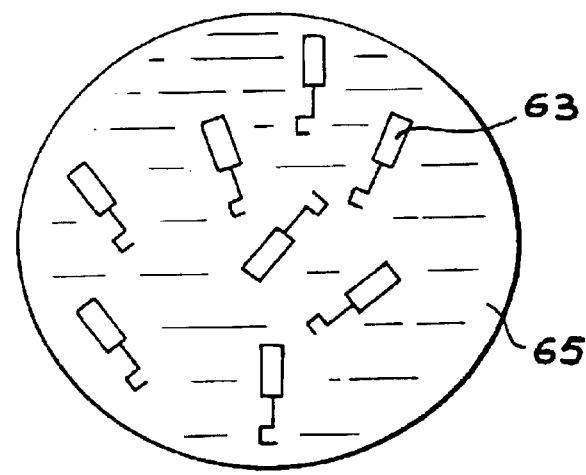
FIG. 5
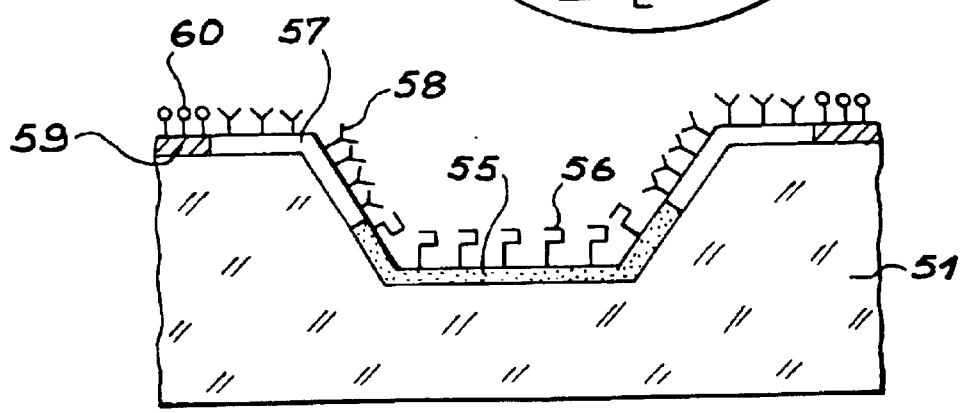

DEVICE COMPRISING A PLURALITY OF ANALYSIS SITES ON A SUPPORT

TECHNICAL FIELD

The subject of the present invention is a device for chemical or biological analysis comprising a large number of analysis sites, which can be used in particular for pharmacological screening and for biological DNA tests.

For screening, on a carrier containing a large number of sites covered with the same reagent, the effect of different molecules must be determined which are selectively deposited on each site in sequential manner.

For biological testing, such as DNA tests, each site of the device is covered with a different DNA probe and the analyte, whose genomic sequence it is desired to determine, is placed in contact at the time of analysis with all the sites.

In analytical chemistry, there is also a strong demand for the miniaturisation of dishes for chemical reaction (or chemical reactors).

For all these applications, it is therefore important to have available a carrier containing the greatest possible number of analysis sites, but a high density of the number of sites raises certain problems of sufficient precision when depositing drops of reagent or samples on the sites.

PRIOR ART

Document U.S. Pat. No. 5,474,796 [1] describes a device containing several analytical sites on the surface of a carrier, in which the sites of analysis are formed by hydrophilic areas separated by hydrophobic areas on a planar carrier.

FIG. 1, appended, shows the structure of this device with its planar carrier 1, on which hydrophilic areas 3 and hydrophobic areas 5 are defined.

These hydrophilic and hydrophobic areas are fabricated on carrier 1 by photomasking, followed by reaction of a hydrophilic or hydrophobic silane with the glass carrier.

In this case, the hydrophilic areas 3 formed by planar areas force the deposited drops of reagent 7 to remain where they are owing to the presence of the adjacent hydrophobic areas 5.

This device is considerably limited by the fact that reagent dispensers do not allow the size of drop 7 to be infinitely reduced.

Therefore, if it is desired to increase the integration and density of the number of sites on the carrier, for example to increase the spacing to less than 300 μm, it is the resolution of the dispenser which currently limits the system, since with lithographic techniques it would be fully possible to limit the surface of the hydrophilic and hydrophobic areas in order to increase site density.

Another important parameter of the system is the effective surface area of the site since the reagent, a DNA probe for example, is brought to the site in a solution which is dried on the site. Therefore, if the effective surface area of the site is reduced, the quantity of reagent after drying becomes very small.

Finally, handling the carrier with drops deposited on its surface is not easy.

The subject of the present invention is precisely a device for chemical or biological analysis with which it is possible to increase the integration and density of the number of sites on a carrier, while using current dispensers whose standard capacity cannot distribute drops smaller than 50 to 1000 picoliters, with good spatial precision of deposits.

DISCLOSURE OF THE INVENTION

The subject of the invention is a device for chemical or biological analysis comprising a carrier containing a plurality of analysis sites able to fix a chemical or biological reagent, in which the analysis sites are made up of microdishes hollowed out of the carrier, the side walls and the bottom of the microdishes and the areas of the carrier surface surrounding each microdish, called microdish edges, being in at least one hydrophilic material or being made hydrophilic by a treatment, and the planar areas of the carrier arranged between the areas surrounding the microdishes being in a hydrophobic material or being made hydrophobic by a treatment.

It is specified that in the description and following claims, the terms " hydrophilic material" mean that the material is hydrophilic or has been made hydrophilic through a treatment.

Similarly, the terms "hydrophobic material" mean that the material is hydrophobic or has been hydrophobic through a treatment.

In this device, the microdishes may, in particular, be in the shape of a flattened cone whose smaller base corresponds to the bottom of the microdish.

In this device, the fact that the microdishes are in a hydrophilic material with areas surrounding the microdishes, or edges, also in hydrophilic material, separated on the surface by a hydrophobic material, means that it is possible to provide a drop anchoring zone within the thickness of the carrier, thereby limiting the diameter of the analysis sites without limiting the volume of the drops. In this way it is possible to reach a higher densification of active sites than with the planar carrier of the prior art.

Therefore, the structure of the invention provides two advantages of interest:

1) it allows the use of droplet dispensers having limited resolution, and
2) it allows the use of droplets having a greater diameter than that of the microdishes which gives a higher concentration of solute after evaporation of the solvent.

According to a first embodiment of the device of the invention, the side walls, the bottom parts and the edges of the microdishes are made in the same hydrophilic material. This makes it possible, in particular, to ensure refocusing and anchoring of the reagent drops in the microdishes and on the edge of the microdishes if the drop overflows the microdish.

According to a second embodiment of the device of the invention, the bottom parts of the microdishes are made in a first hydrophilic material, and at least part of the side walls of the microdishes and the edges of the microdishes are made in a second hydrophilic material, solely the first hydrophilic material being able to fix the chemical or biological reagent.

With this special structure it is possible to attract the drop into the microdish by means of the second hydrophilic material and to ensure fixing of the reagent in the bottom of the microdish by means of the first hydrophilic material. This provision is of particular interest if the reagent is diluted in an aqueous solution. By making microdishes it is possible to observe fluorescence at the analysis stage in a plane that is different to the plane of the substrate which often generates an interference signal (fluorescence) intrinsic to the nature of the substrate.

Therefore, the drop of aqueous solution will moisten the second hydrophilic material but the reagent present in a small quantity will be fixed to the bottom of the microdish.

According to the invention, the carrier for the system may be a passive substrate in glass, silicon, or an organic polymer, having no particular function. In the invention it is also possible to use a carrier which contains an active substrate with an integrated electronic system having various electronic functions, site addressing for example, localised heating or CCD for integrated detection of fluorescence.

An active substrate of this type is described for example in the document by Eggers et al., A versatile biochip for gene-based diagnotics, 1996, IEEE, p. 87–92 [2]. For such carriers, the active substrate is generally coated with a polymer layer in which the microdishes are formed.

In the system of the invention, the hydrophilic materials) may be materials comprising hydrophilic groups chosen from among the epoxy groups, —OH, —SH, —NH—, —NH2 and —COOH.

The hydrophobic material may be formed by the carrier itself for a carrier in hydrophobic organic polymer, or it may be formed on the carrier. Generally, the hydrophobic material comprises hydrocarbon-containing or fluorocarbon-containing groups.

The base material used, glass or silicon, may be made selectively hydrophilic or hydrophobic using a suitable surface treatment.

A further subject of the invention is a method for producing a device for chemical or biological analysis such as described above.

According to a first embodiment, this method comprises the following steps:
a) hollowing out microdishes (or microwells or microcavities) on the surface of the carrier,
b) defining the areas of the carrier surface which are to comprise a hydrophobic material, and
c) then forming a hydrophilic material on the areas of the carrier surface and of the microdishes which do not contain any hydrophobic material.

According to one variant of this first embodiment, the method entails the following steps:
a) hollowing out microdishes on the surface of the carrier, and
b) forming a hydrophilic material on the areas of the carrier surface which are to contain a hydrophilic material.

The methods described above are appropriate for producing microdishes whose side walls, bottom parts and edges are made in the same hydrophilic material.

According to a second embodiment of the method of the invention adapted to the formation of microdishes comprising two different hydrophilic materials, the method advantageously entails the following steps:
a) hollowing out microdishes on the carrier surface,
b) defining the areas of the carrier surface which are to comprise a hydrophobic material,
c) then, on the carrier surface not comprising any hydrophobic material and on the surface of the microdishes, defining first areas corresponding to the positioning of the first hydrophilic material and second areas corresponding to the positioning of the second hydrophilic material, and
d) forming the first hydrophilic material on the first areas and the second hydrophilic material on the second areas.

If the carrier is in a non-hydrophobic material, the method also comprises an additional step to form a hydrophobic material on the areas of the carrier surface which are to comprise a hydrophobic material.

To apply the method of the invention, first the microdishes are hollowed out in the thickness of the carrier. Conventional lithography techniques followed by dry or chemical etching may be used for this operation.

If the carrier is in silicon, the microdishes may be made by preferential chemical etching of crystalline planes, which gives a microdish with a 54° slope and a flat bottom. The spacing or pitch of the microdishes may range from 10 to 500 μm and the depth of the microdishes may range from 5 to 500 μm. Generally a lithography technique is used to define the microdishes at the desired positions.

For glass carriers, the microdishes may be made by dry isotropic etching, with no angles, also using a lithography technique to define the positions of the microdishes.

If the carrier comprises an active substrate with an electronic function, the carrier is preferably provided on its upper surface with a polymer or mineral oxide layer in which the microdishes are made by etching, also using a lithography technique to define the positions of the microdishes.

At all events, microdishes of 5 to 500 μm in depth can be obtained, with a microdish pitch of 10 to 500 μm, and a microdish upper opening of 3 to 450 μm.

The subsequent steps of the method consist of forming the areas of hydrophobic material and the areas of hydrophilic material(s) on the surface of the carrier.

These areas may be formed by modifying the surface of the carrier by grafting hydrophobic or hydrophilic groups.

However, if the carrier is in a hydrophobic organic polymer, or coated with a hydrophobic organic polymer, it is not necessary to modify the surface of the carrier to create the hydrophobic areas.

If the carrier is in silicon or glass, this modification may be made by causing the silicon or glass to react with a hydrophobic or hydrophilic silanisation agent.

If the carrier is in silicon, it is previously subjected to oxidation followed by a conventional cleaning treatment (e.g.: HCl) to obtain OH groups on the surface enabling the reaction with the silanisation agent.

The hydrophobic silanisation agent may be a silane having the formula:

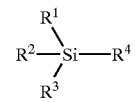

in which $R^1$, $R^2$ and $R^3$ which may be identical or different, are chosen from among the $C_1$ to $C_3$ alkoxy groups and the halogen atoms (preferably chlorine), and $R^4$ is a hydrocarbon-containing or fluorocarbon-containing group, either linear or branched.

Preferably, the hydrocarbon or fluorocarbon group contains 4 to 18 carbon atoms.

As examples of hydrophobic silanisation agents, the following compounds may be cited:
a commercially available product called "Repelsilane",
octadecyl triethoxysilane
tridecafluoro-1,1,2,2-tetrahydrooctyldimethyl chlorosilane,
3-(1,1-dihydroperfluoroctyloxy) propyltriethoxysilane,
hexamethyl disilazane (HMDS).

The hydrophilic silanisation agent may be a silane having the formula:

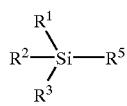

in which $R^1$, $R^2$ and $R^3$, which may be identical or different, are chosen from among the $C_1$ to $C_3$ alcoxy groups and the halogen atoms, preferably chlorine, and $R^5$ is a linear or branched hydrocarbon group containing at least one hydrophilic group chosen from among the epoxy groups —OH, —SH, —NH$_2$, —NH— and —COOH.

The hydrocarbon group advantageously has 3 to 18 carbon atoms.

As examples of hydrophilic silanisation agents, the following compounds may be cited:

aminopropyl trimethoxysilane "γ APS", trimethoxysilylpropyl-ditheyenetriamine "DETA"

N-(2-aminoethyl)-3-aminopropyltrimethoxy-silane "EDA"

N,N-bis (hydroxyethyl) aminopropyltriethoxy-silane the commercial product called "Bind Silane"

aminoethylaminomethyl phenetyl trimethoxysilane "PEDEA" or further mercaptopropyl-trimethoxysilane

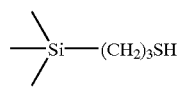

It is also possible to form the hydrophobic material and/or the hydrophilic material on the carrier using thiols or disulfides to add the hydrophilic or hydrophobic groups. In this case, firstly a metallic layer in gold, silver or copper or one of their alloys is deposited on the areas to be modified, and this layer is then caused to react with a thiol or a disulfide containing one or more hydrophilic or hydrophobic groups. As previously, the hydrophobic groups may be hydrocarbon or fluorocarbon-containing groups, either linear or branched. The hydrophilic groups may be chosen from among the epoxy groups, —OH, —NH—, —NH$_2$, —COOH and —SH.

To functionalise Au, AG, Cu, as examples of thiols and disulfides which may be used, mention may be made of the following compounds:

octadecane thiol, R—SH(R=CB to $C_{18}$), hydrophobic hexadecane thiol 3-mercaptopropionic acid →hydrophilic (to render the gold hydrophilic).

According to the method of the invention, the areas of hydrophilic material(s) or made hydrophilic and the areas of hydrophobic material or made hydrophobic can be defined on the carrier using conventional microelectronic techniques, for example lithography methods using negative or positive photoresists, with masking and resin development. The developed areas are treated, then the resin is removed and the exposed areas are treated by another silanisation agent.

Therefore, according to the invention, the hydrophilic and hydrophobic areas may be formed on the carrier using etching methods, by treating for example all the surface of the carrier to make it hydrophilic or hydrophobic, and then removing the hydrophilic or hydrophobic material on some areas of the carrier, for example by means of a laser. The exposed areas can then be treated to form the desired hydrophobic or hydrophilic areas.

Other characteristics and advantages of the invention will become better apparent on reading the following description, evidently given by way of illustration and non-restrictive, with reference to the appended drawings.

SHORT DESCRIPTION OF THE DRAWINGS

FIG. 1, already described, is a diagram of a device according to the prior art.

FIGS. 4A and 4B illustrate the placing of a drop of reagent in a device of the invention.

FIGS. 5 to 7 illustrate the advantage of the second embodiment of the device of the invention to cause the biological reagent to adhere to the bottom of the microdish.

DETAILED DESCRIPTION OF THE EMBODIMENTS

Figure 1:
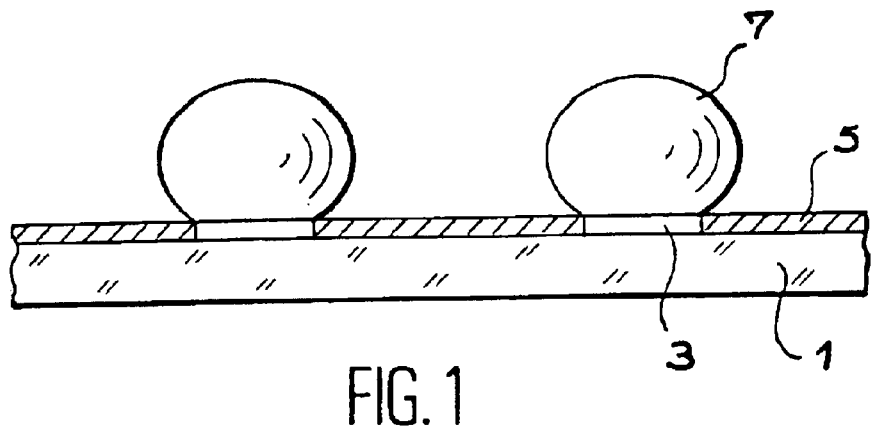
Figure 2:
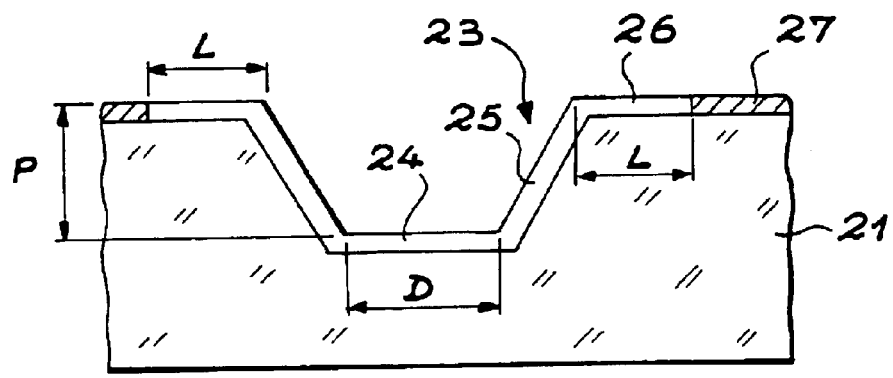
FIG. 2 illustrates the first embodiment of the device of the invention.

FIG. 2 shows the first embodiment of the device of the invention, in which a single hydrophilic material is used.

In this figure, carrier 21 can be seen in which the microdishes 23 are hollowed out and have a flattened cone shape whose smaller base corresponds to the bottom 24 of the microdish. In the first embodiment of the invention, bottom parts 24, side walls 25 and the areas of the carrier surface surrounding each microdish, hereinafter called edges 26 of the microdishes, are formed of hydrophilic material, whereas the surface of the carrier located between the edges of the microdishes is formed of hydrophobic material 27.

Figure 3:
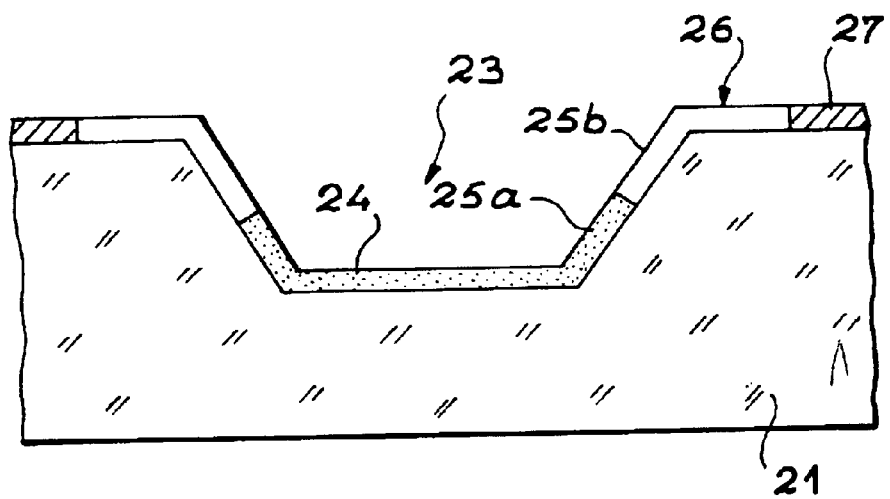
FIG. 3 illustrates the second embodiment of the device of the invention.

FIG. 3 is a diagram of the second embodiment of the device of the invention, in which two different hydrophilic materials are used.

In this figure the same references are used to designate the carrier 21, the microdishes 23 and the areas of hydrophobic material 27. In this case, the bottoms 24 of the microdishes and part of their side walls 25a are made in a first hydrophilic material whereas the remainder of their side walls 25b and the edges 26 are made in a second hydrophilic material. This makes it possible, as will be seen later, to achieve adhesion of the chemical or biological reagent to the bottom of the microdishes.

In these two embodiments of the device of the invention, the three-dimensional structuring of the carrier leads to obtaining numerous advantages.

With this structuring it is possible to limit the surface of the reactive sites corresponding to the opening of the microdishes, since the latter are hollowed in the thickness of the carrier and can contain more reagent or sample for a smaller effective surface area.

Therefore, it is possible to reduce the pitch and size of the microdishes to micronic sizes without being limited either by the positioning precision of the robot dispensing the reagent or sample, or by the volume of the drops. Moreover, by providing hydrophilic areas around the microdishes and in the microdishes in contrast to the remainder of the carrier that is hydrophobic, it is possible for the drops to be anchored and guided into the microdish as can be seen in FIGS. 4A and 4B.

With reference to FIG. 4A, the device according to the first embodiment of the invention can be seen, which comprises a carrier 21 provided with microdishes 23 having hydrophilic areas 24 and hydrophobic areas 27.

FIG. 4A shows the device at the feeding stage of the drops 29 of reagent or sample which may be deposited by a microdispenser (micropipeting robot) or inkjet print-heads.

As can be seen in FIG. 4A, the drops are not necessarily positioned perpendicular to the microdish openings. But the presence of hydrophilic areas 24 and hydrophobic areas 27 allows the anchoring and guiding of the drop into the microdish. On account of the surface tensions set up by the hydrophilic properties of the surface, the deposited drop is able to slide into position and fill the microdishes perfectly as shown in FIG. 4B. Therefore, for a given drop size, the pitch of the reagent sites can be reduced on the carrier with no risk of bridging between drops and therefore of reagent mixing. Also, even if drop positioning is imperfect, it is possible to achieve perfect spatial distribution as provided by the positioning of the microdishes which may be extremely precise through the use of micro-machining, as will be seen below.

With this device it is also to be noted that the ratio of volume/surface in contact with the reagent is increased for identical occupation of space. This means that if the reagent contains substances which are to be fixed after drying on the hydrophilic zone, they will be much greater in number.

Also, this type of structure can be added above an active substrate, for example a DNA chip with integrated heating or reading means.

Finally this structure of the device of the invention is compatible with localised in situ DNA synthesis methods. Once the first base of the probe is fixed in the microdishes, the probe can be constructed base after base in these microdishes.

Figure 6:
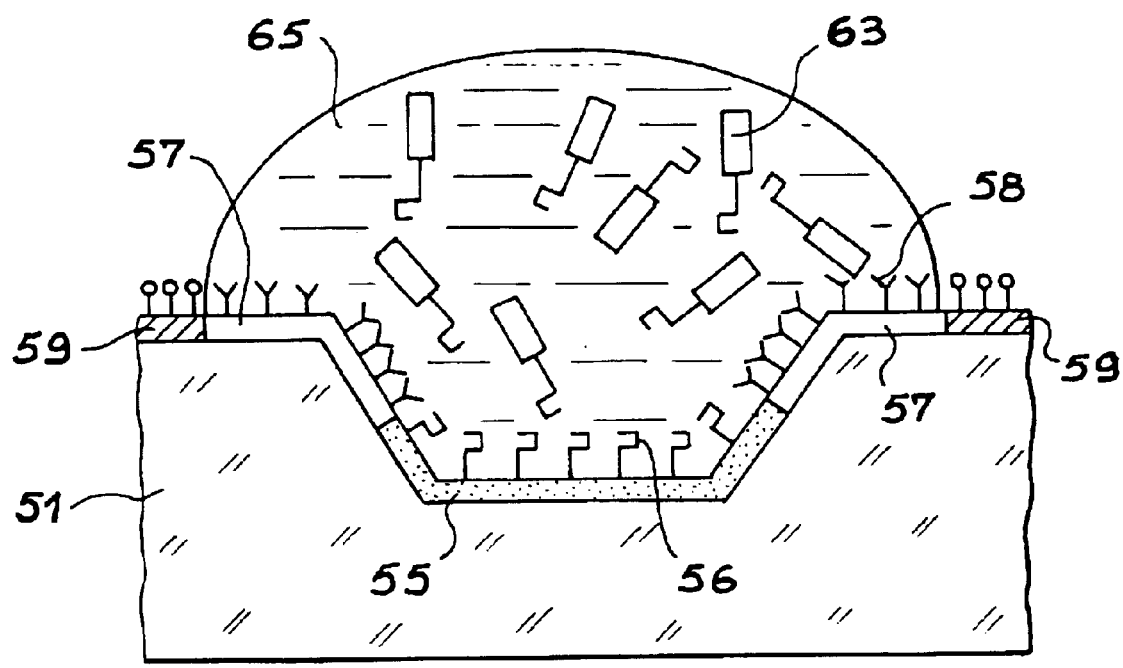
Figure 7:
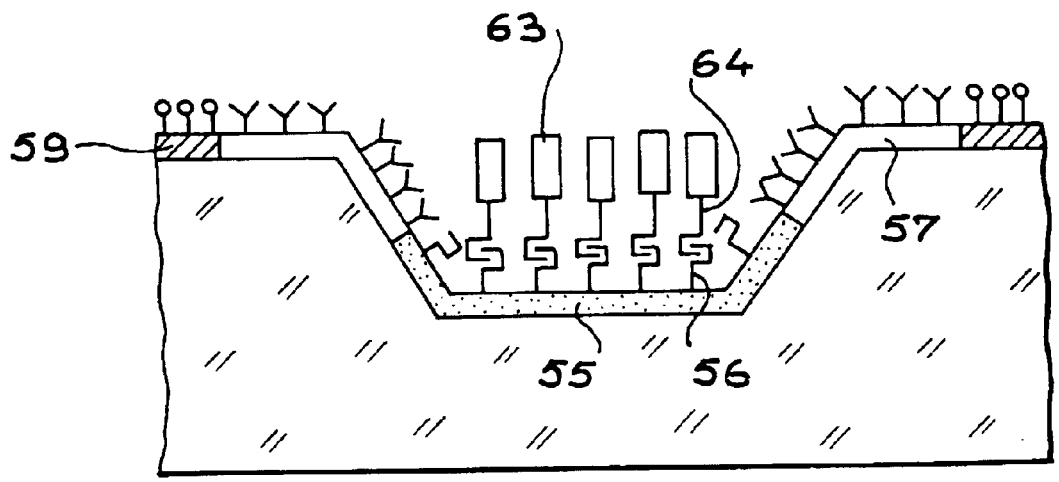

FIGS. 5 to 7 show the advantage of using a device according to the second embodiment of the device of the invention, to produce DNA chips.

In FIG. 5 one of the microdishes of the device can be seen, which comprises a carrier 51 provided with microdishes 53 with the presence of a first hydrophilic material 55 and a second hydrophilic material 57 in the microdishes and on their edges, and a hydrophobic material 59 between the microdishes.

This figure illustrates the hydrophilic groups 56 of the first hydrophilic material, the hydrophilic groups 58 of the second hydrophilic material and the hydrophobic groups 60 of the hydrophobic material. It will be observed that the hydrophilic groups 56 are different to hydrophilic groups 58, hydrophilic groups 56 being chosen to fix the reagent, for example the nucleic probes 63 present in the drop of reagent 65. FIG. 5 therefore corresponds to the drop-feeding step of the device.

FIG. 6 illustrates the refocusing phase of drop 65 on the hydrophilic areas on account of repelling in hydrophobic areas 59.

FIG. 7 illustrates the fixation step of nucleic probes 63 on the first hydrophilic material 55 by reaction of the hydrophilic groups 64 of the probe with the hydrophilic groups 56 of the first hydrophilic material 55.

By way of example, the nucleotide probe may be functionalised with an OH group and the first hydrophilic material 55 may contain OH hydrophilic groups, while the second hydrophilic material contains COOH or $NH_2$ hydrophilic groups. In this manner, there will only be probe coupling on the first hydrophilic material 55.

A fixation technique for oligonucleotide probes on glass surfaces previously modified by silanisation is described by Beattie et al in Clin. Chem., vol. 39, No 4, 1993, pages 714–722 [3].

This embodiment of the device of the invention is of particular interest since if the pitch of the microdishes is reduced, the sites covered by the different reagents become very close to one another which raises problems for detection if fluorescence is used to read results. By permitting the use of relatively voluminous drops while maintaining sufficient space between reagent sites, the chain of acquisition is simplified.

Moreover, with this improvement, reagent is only obtained in the bottom of the microdishes, which makes it possible to situate the site of any chemical reaction on a different plane. This may be used by a reading system to overcome interfering fluorescence on the surface of the carrier for example (differential focusing).

The microdishes described above are able to receive mechanically-dispensed drops. It has been seen that two particular advantages of the invention must be taken into account:
  overcoming the intrinsic precision of the dispenser: even an ill-adjusted drop "falls" into the microdish on account of the hydrophilic area (26 or 57) which extends over the planar part of the carrier around each dish.
  allowing a substantial quantity of reagent contained in the drop to fix itself in the dish. A drop that is much more voluminous than the dish may be deposited, as it will be centered over the dish by the hydrophilic areas extending around the dish. This is of great importance as the reagents contained in the drop cannot be too concentrated otherwise dispensing problems will arise.

Concerning topology, and as an illustration, two types of dishes were made having the following sizes as shown in FIG. 2:
1) Dish diameter at bottom of hollow D: 100 µm
   Dish depth P: 30 µm
   Area extending over the planar part on each side L: 15 µm
   Pitch: 180 µm
2) Dish diameter at bottom of hollow D: 70 µm
   Dish depth P: 20 µm
   Area extending over the planar part on each side L: 10 µm
   Pitch: 140 µm.

FIGS. 8A to 8E illustrate the different steps in producing a device of the invention, using a single hydrophilic material, and in which the hydrophilic and hydrophobic areas are formed by silanisation, the carrier being in silicon.

Figure 8:
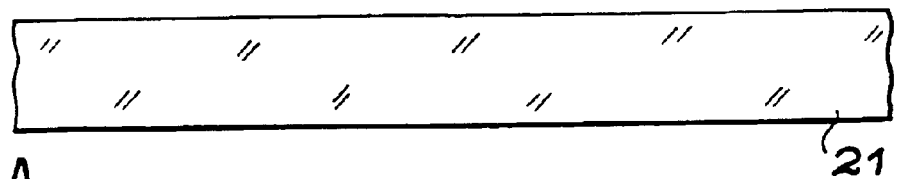
FIGS. 8A to 8E illustrate the different steps of the production process for the device of the invention, when silanisation is used to make the hydrophobic and hydrophilic areas.
Figure 8:
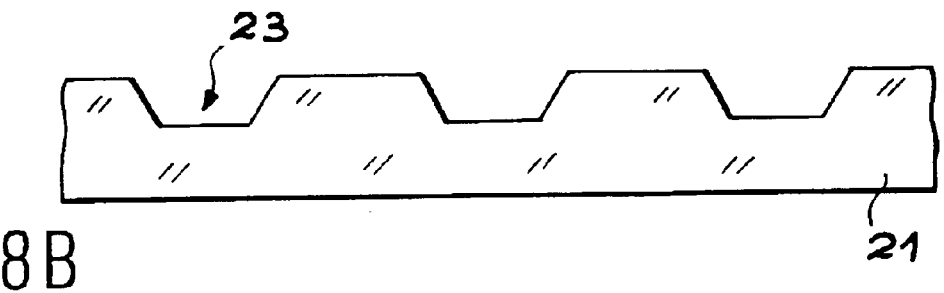
Figure 8:
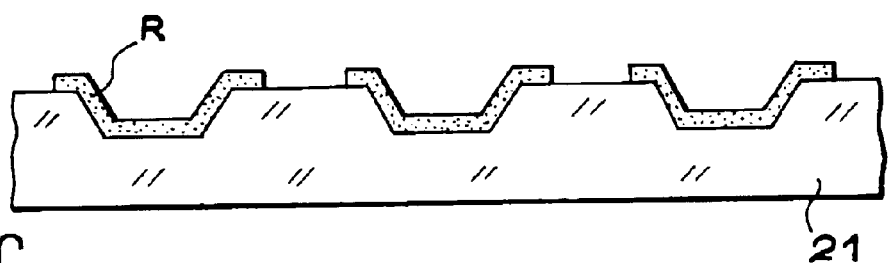
Figure 8:
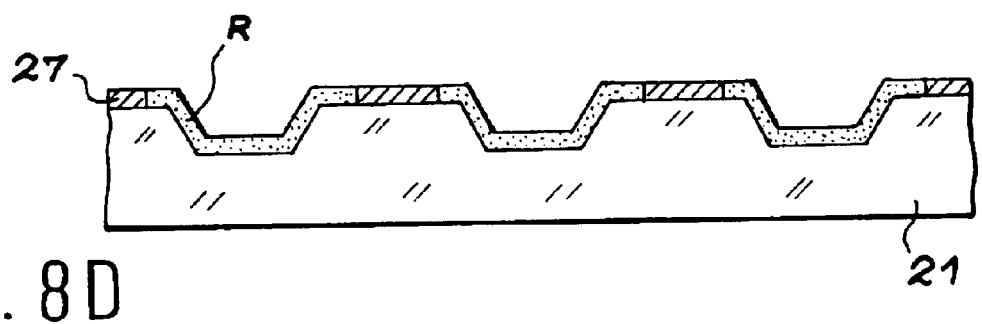
Figure 8:
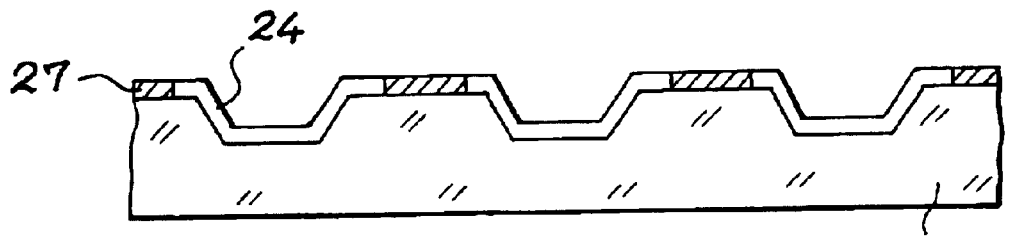

In FIG. 8A, the initial carrier 21 in silicon can be seen.

FIG. 8B shows the formation step of the microdishes 23 in carrier 21. This may be made by lithography and chemical etching along crystalline planes. In this manner microdishes of flattened cone shape are obtained with a slope of 54° and a flat bottom. The pitch of the microdishes may range from 10 to 500 µm and their depth from 5 to 500 µm, in order to adapt to the sizes of the drops dispensed by the automatons depositing the reagents.

After lithography of the microdishes, the unit is subjected to heat oxidation treatment at a temperature of more than 800° C., for example 850° C., to obtain OH groups on the silicon surface.

FIG. 8C shows the step during which areas of hydrophobic material are defined using a mask. This mask may be formed of a photosensitive resin R which is deposited on the carrier, and which is subsequently exposed to obtain the required pattern and developed to uncover the areas which are to be hydrophobic. Resin R may be any photoresist used in microelectronics. In particular the positive Shippley resin (S1813 or STR1075) or negative resin SAL 601 may be used and the Microposit MF 319 developer.

FIG. 8D shows the step for creating areas of hydrophobic material 27 by hydrophobic silanisation of the silicon carrier exposed by means of the silanisation agent, for example tridecafluoro-tetrahydro-octyltriethoxy-silane (also called F13).

After creating the areas of hydrophobic material 27, resin R is removed by dissolution, for example in acetone to expose the areas which are to contain the hydrophilic material.

FIG. 8E shows the production of these areas in hydrophilic material 24 by hydrophilic silanisation using EDA, γAPS or DETA.

FIGS. 9A to 9D show a variant of embodiment of the device of the invention with a carrier in silicon coated with gold plating, in which thiols are used to create the hydrophilic material and hydrophobic material. In this case, as previously, microdishes of flattened cone shape 23 are hollowed out of the silicon carrier 21 by chemical litho-etching along crystalline planes, then gold is deposited on the entire carrier to form a layer having a thickness of 50 to 5000 $\mu$m.

Figure 9A:
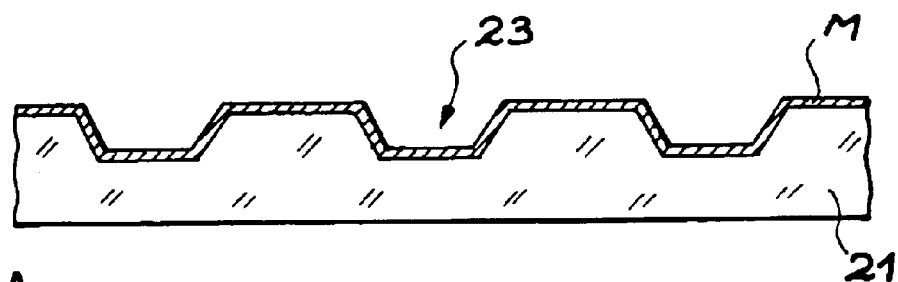
FIGS. 9A to 9D illustrate the different steps of the production process for a device of the invention using thiols to form the hydrophilic and hydrophobic areas.

FIG. 9A shows the carrier 21 provided with microdishes 23 and coated with a gold layer M.

After the microdishes have been formed, the areas of hydrophobic material are defined by lithography using a photosensitive resin R as described previously.

Figure 9B:
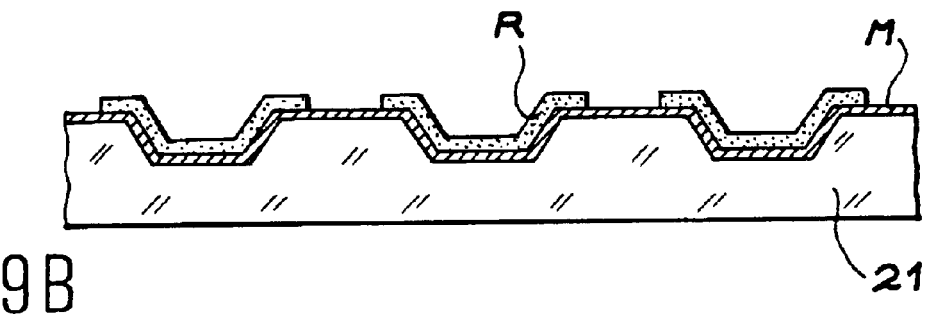

In this way the structure shown in FIG. 9B is obtained in which the gold layer M is uncovered on the areas which are to be hydrophobic.

The hydrophobic material is then formed by reaction of the exposed gold deposit with a hydrophobic thiol such as octadecane thiol $CH_3-(CH_2)17-SH$.

Figure 9C:
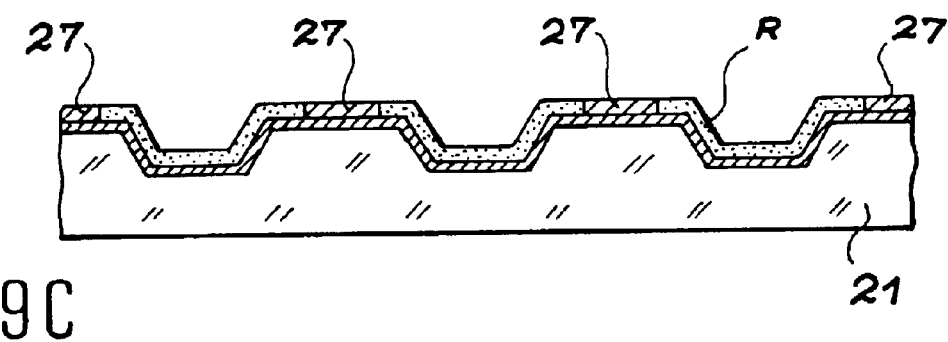

This gives the structure shown in FIG. 9C with the areas of hydrophobic material 27. After this operation, the layer of resin R is removed as previously by dissolution in acetone and the uncovered areas are treated with a hydrophilic thiol. As hydrophilic thiol $HO(CH_2)_nSH$, $HOOC(CH_2)_nSH$ may be used (n=3 to 18).

Figure 9D:
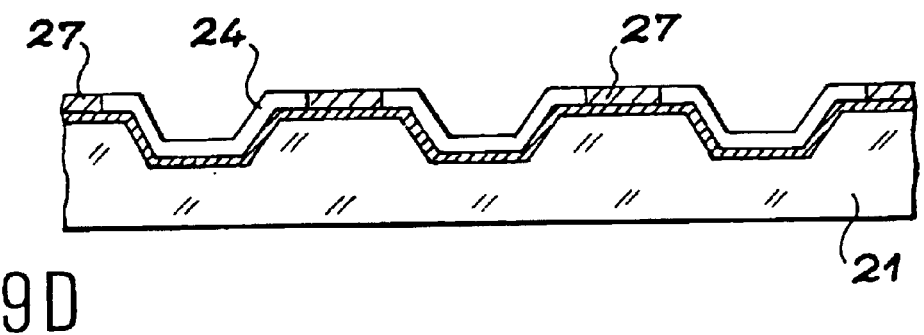

In this way the structure shown in FIG. 9D is obtained, comprising areas of hydrophilic material 24 separated by areas of hydrophobic material 27.

Although in the two above-described examples hydrophobic and hydrophilic materials have been made by a silanisation treatment or modification by means of a thiol, it is evidently possible to combine these two possible modifications of the carrier surface by creating some areas by silanisation and other areas by reaction of the carrier with a thiol, or by other hydrophilisation or hydrophobisation techniques.

If the carrier is in glass, the microdishes may be formed by angle-free isotropic etching, and then the areas of hydrophilic material and the areas of hydrophobic material may be formed using the methods described above. If these areas are formed by silanisation, it is not necessary to subject the carrier to oxidation after etching the microdishes, since glass has the necessary OH functions for the following steps. It is also possible, for glass substrates, to make the areas of hydrophilic material and hydrophobic material after depositing gold by reaction with a thiol and to combine these methods.

The advantage of a glass substrate is that it allows the microdishes to be made by isotropic etching, which leads to obtaining angle-free microdishes thereby facilitating the various rinsing operations.

As seen previously, the invention may also be implemented on a carrier comprising an active substrate with integrated electronics. This type of substrate enables localised heating of the sites or CCD reading of reagent-electrolyte pairing to be analysed on these sites, or the addressing of each site to apply a voltage for example. The active substrate may be made in silicon or glass using flat panel techniques.

In this case, the structure of the invention is constructed over the finished active carrier by coating the latter with a layer of mineral oxide or a polymer layer, the deposited layer being sufficiently thick to form microdishes of desired depth.

After forming the microdishes in this layer of polymer of mineral oxide, the hydrophilic areas, and hydrophobic areas can be defined as previously by reaction of a gold layer with a thiol. For a polymer layer, the hydrophobic areas may also be formed by the polymer layer.

Figure 10:
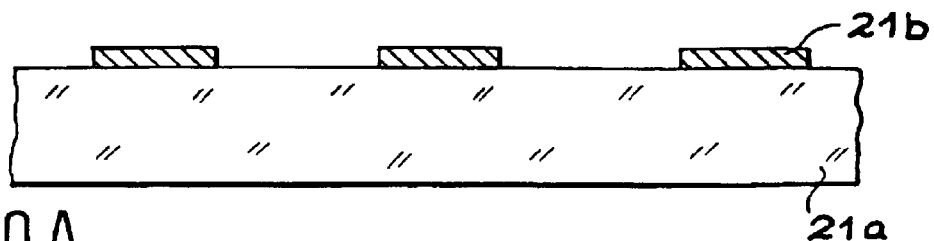
FIGS. 10A to 10C illustrate the steps in the production process of a device of the invention using an active substrate having electronic functions, coated with a hydrophobic polymer layer.
Figure 10:
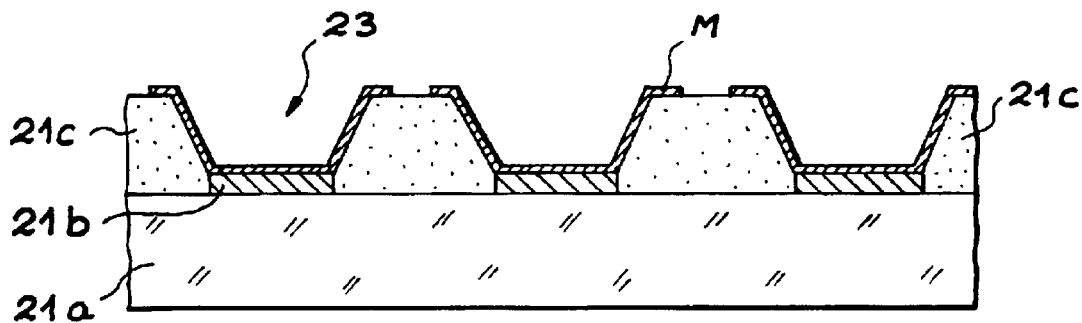
Figure 10:
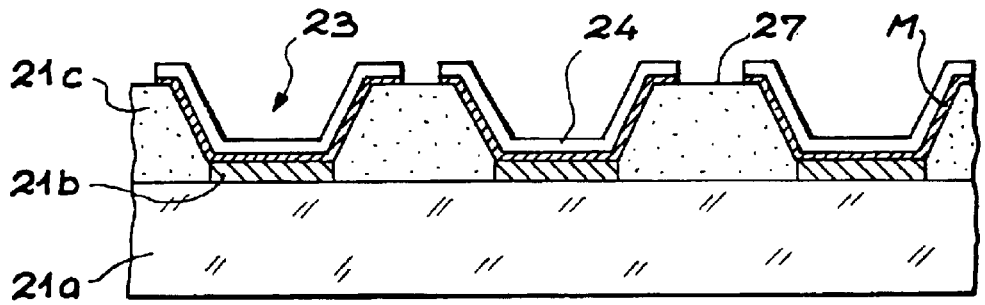

FIGS. 10A to 10C illustrate the steps for producing this device.

FIG. 10A shows the active substrate 21a provided with surface pads 21b at positions which correspond to the sites of analysis.

On this carrier 21a, first of all a thick layer of polymer 21c is deposited, a polyimide for example having a thickness of 5 to 100 $\mu$m, then the microdishes 23 are hollowed out of this layer by lithography, casting, . . .

On the areas of the carrier which are to be in hydrophilic material, a layer of gold M is subsequently deposited so as to define the hydrophilic layers.

FIG. 10B shows the structure obtained which comprises the active substrate 21a, the surface pads 21b, the polymer layer 21c, the microdishes 23 and the gold layer M.

FIG. 10c shows the step for forming the hydrophilic areas by treating the entire unit with hydrophilic thiol which fixes itself to the gold M to form the areas of hydrophilic material 24.

In this case, it is not necessary to make areas of hydrophobic material, the latter being formed by the layer of polymer 21c remaining between the microdishes 23.

FIGS. 11A to 11G show the different steps of the production process for a device according to the second embodiment of the invention, comprising two types of hydrophilic materials.

Figure 11:
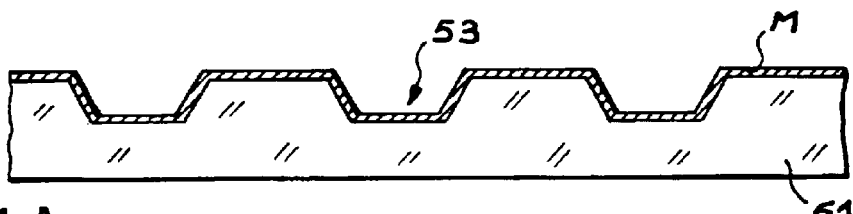
FIGS. 11A to 11G illustrate the different steps of the production process for a device according to the second embodiment of the invention.
Figure 11:
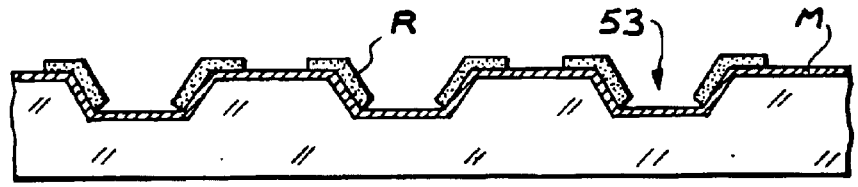

In this case, as shown in FIG. 11A, a carrier 51 is used in silicon for example in which the microdishes 53 of flattened cone shape are made by litho-etching as in the first embodiment. Then a gold layer M is deposited on the entire unit.

FIG. 11B shows the structure of the carrier after depositing a resin R at the places which correspond to the areas which are to comprise the second hydrophilic material.

Figure 11C:
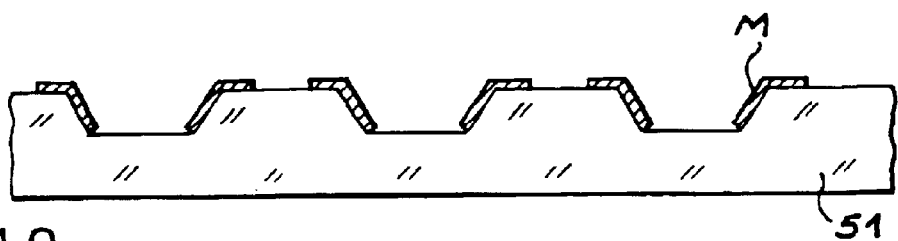

FIG. 11C shows the structure obtained after etching of the gold to remove the gold layer on the areas corresponding to the hydrophobic material and on the areas corresponding to the first hydrophilic material, and after removing the resin R from the areas corresponding to the second hydrophilic material.

Figure 11D:
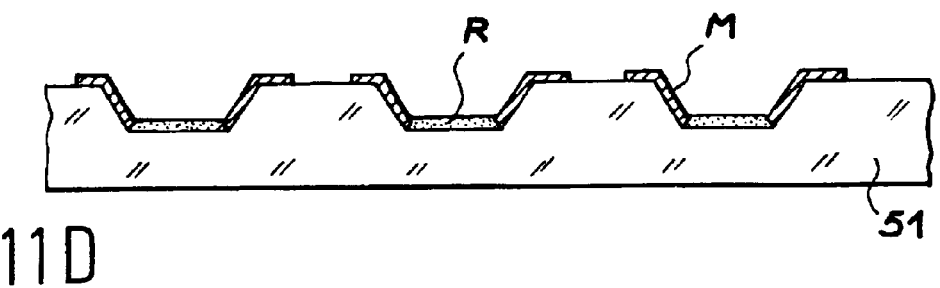

FIG. 11D shows the structure obtained after protecting the bottoms of the microdishes by a resin R identical or different to the first resin R. This protection may be achieved using a lithography technique by depositing a photosensitive resin exposed at the desired sites which is then removed from the desired areas.

Figure 11E:
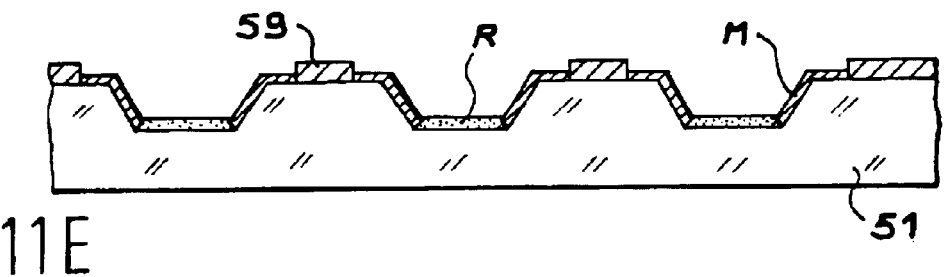

FIG. 11E shows the creation of areas of hydrophobic material 59 which are formed by hydrophobic silanisation of the carrier by means of Repel Silane.

Figure 11F:
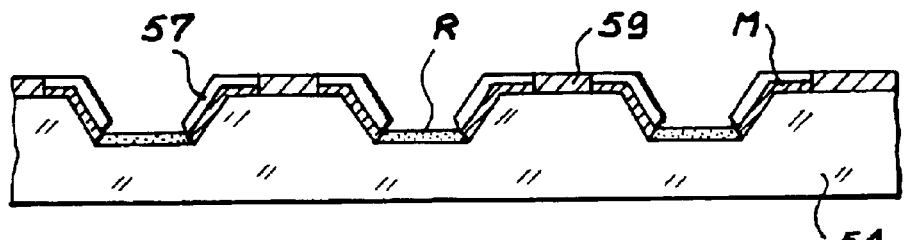

FIG. 11F shows the creation of areas 57 of the second hydrophilic material by reaction of the gold with a hydrophilic thiol containing COOH or $NH_2$ groups, for example $HOOC-(CH_2)_2-SH$.

Figure 11G:
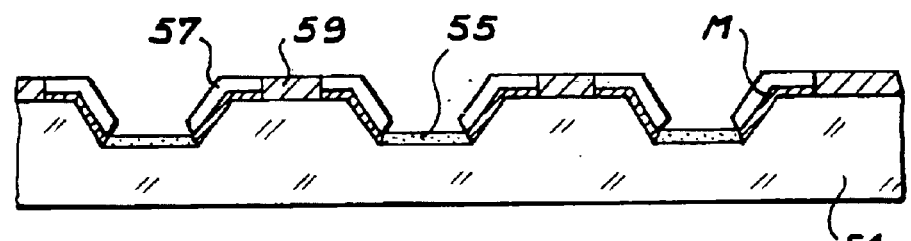

FIG. 11G shows the final structure obtained after removing the resin R from the bottom of the microdishes and after subjecting the carrier to a silanisation treatment using $OH(CH_2)_{16}-SH$.

Therefore, with the silanisation treatment, a first hydrophilic material 55 is obtained containing OH hydrophilic groups, whereas the areas 57 of the second hydrophilic material contain COOH hydrophilic groups. Hence, by using a reagent with OH groups such as an oligonucleotide, a linker or a precursor of nucleotide synthesis, functionalised with an OH group, it is possible to fix this reagent preferentially in the bottom of the microdishes.

Evidently, in the example of embodiment described above, the order of the steps could be different. Similarly, other techniques could be used to respectively create areas 57 and 55 of the first and second hydrophilic material, and to abolish the step for creating areas 59 of hydrophobic material if the carrier is hydrophobic.

CITED REFERENCES

[1] U.S. Pat. No. 5,474,796
[2] Eggers et al., A versatile biochip for gene-based diagnotics, 0-7803-3271-7/96, 1996, IEEE, p. 87–92
[3] Beattie et al., Clin. Chem., vol. 39, no 4, 1993, pages 719–722.

What is claimed is:

1. A device for chemical or biological analysis comprising a carrier comprising a plurality of analysis sites able to fix a chemical or biological reagent, wherein the analysis sites are formed of microdishes hollowed out of the carrier, the side walls and the bottom of the microdishes and the areas of the carrier surface surrounding each microdish, called microdish edges, being made in at least one hydrophilic material and the planar areas of the carrier arranged between the areas surrounding the microdishes being made in a hydrophobic material;
   wherein the bottoms of the microdishes are made in a first hydrophilic material, and at least part of the side walls of the microdishes and the edges of the microdishes are made in a second hydrophilic material, solely the first hydrophilic material being able to fix the chemical or biological reagent.

2. The device according to claim 1, wherein the microdishes have the shape of a flattened cone whose smaller base corresponds to the bottom of the microdish.

3. The device according to claim 1, wherein the at least one hydrophilic material comprises at least one hydrophilic group selected from the group consisting of an epoxy group, —OH, —SH, —NH—, —NH$_2$, —COOH and combinations thereof.

4. The device according to claim 1, wherein the at least one hydrophobic material comprises at least one hydrophobic group selected from the group consisting of a hydrocarbon-containing group, a fluorocarbon-containing group, and combinations thereof.

5. The device according to claim 1, wherein the first hydrophilic material comprises hydrophilic groups different to those of the second hydrophilic material.

6. The device according to claim 1, wherein the carrier comprises an active substrate with an integrated electronic system having electronic functions.

7. The device according to claim 1, wherein the biological reagent is an oligonucleotide.

8. A method for producing a device for chemical or biological analysis according to claim 1, which comprises the following steps:
   a) hollowing out microdishes on the surface of the carrier,
   b) defining the areas of the carrier surface which are to contain a hydrophobic material,
   c) defining, on the carrier surface not comprising any hydrophobic material and on the surface of the microdishes, first areas corresponding to the sites of the first hydrophilic material and second areas corresponding to the sites of the second hydrophilic material, and
   d) forming the first hydrophilic material on the first areas and the second hydrophilic material on the second areas.

9. The method according to claim 8, further comprising:
   forming a hydrophobic material on the areas of the carrier surface which are to contain a hydrophobic material.

10. The method according to claim 8, wherein the microdishes are formed by etching.

11. The method according to claim 8, wherein the carrier comprises a surface layer in a polymer or a mineral oxide deposited on an active substrate having an electronic function, and the microdishes are made by etching in the polymer or oxide layer.

12. The method according to claim 9, wherein the carrier being in silicon or in glass, the hydrophobic material is formed by reaction of the glass or silicon, previously subjected to oxidation, with a hydrophobic silanisation agent.

13. The method according to claim 12, wherein the hydrophobic silanisation agent is a silane having the formula:

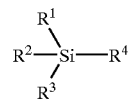

wherein R$^1$, R$^2$ and R$^3$, which may be identical or different, are selected from the the group consisting of a C$_1$ to C$_3$ alkoxy group, a halogen atom, and combinations thereof; and R$^4$ is a hydrocarbon-containing or or fluorocarbon-containing group, either linear or branched.

14. The method according to claim 8, wherein the carrier being in silicon or in glass, the hydrophilic material is formed by reaction of the glass or silicon, previously subjected to oxidation, with a hydrophilic silanisation agent.

15. The method according to claim 14, wherein the hydrophilic silanisation agent is a silane having the formula:

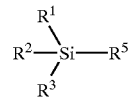

wherein R$^1$, R$^2$ and R$^3$, which may be identical or different, are selected from the group consisting of a C$_1$ to C$_3$ alkoxy group, a halogen atom, and combinations thereof; and R$^5$ is a hydrocarbon- or fluorocarbon-containing group, either linear or branched, comprising at least one hydrophilic group the selected from the group consisting of an epoxy group, —OH, —SH, —NH$_2$, —NH—, COOH, and combinations thereof.

16. The method according to claim 9, wherein the hydrophobic material is formed by reaction of a metallic layer in gold, silver, copper or one of their alloys, deposited on the areas of the carrier surface which are to be formed of hydrophobic material, by reaction of this layer with a thiol or a disulfide comprising a hydrophobic hydrocarbon-containing group or fluorocarbon containing group.

17. The method according to claim 8, wherein the hydrophilic material is formed by reaction of a metallic layer in gold, silver, copper or one of their alloys, deposited on the areas of the carrier which are to be formed of the hydrophilic material, by reaction of this layer with a thiol or a disulfide comprising at least one hydrophilic group the selected from the group consisting of an epoxy group, —OH, —SH, —NH—, —NH$_2$, —COOH and combinations thereof.

* * * * *